United States Patent
Hendriks et al.

[11] Patent Number: 6,024,918
[45] Date of Patent: Feb. 15, 2000

[54] METHOD FOR ATTACHMENT OF BIOMOLECULES TO SURFACES OF MEDICAL DEVICES

[75] Inventors: Marc Hendriks, Brunssum; Michel Verhoeven, Maastricht; Patrick Cahalan; Linda Cahalan, both of Geleen; Edouard Koulik, Maastricht; Mirian Gillissen, Valkenburg A/D Geul, all of Netherlands

[73] Assignee: Medtronic, Inc., Minneapolis, Minn.

[21] Appl. No.: 09/041,497

[22] Filed: Mar. 13, 1998

[51] Int. Cl.[7] ............................. A61M 1/14; A61M 37/00
[52] U.S. Cl. .................................................. 422/44; 604/4
[58] Field of Search ................. 604/4, 5; 422/44

[56] References Cited

U.S. PATENT DOCUMENTS

| | | | |
|---|---|---|---|
| 3,574,673 | 4/1971 | Schweiger | 117/132 |
| 4,239,729 | 12/1980 | Hasegawa et al. | 422/48 |
| 4,600,613 | 7/1986 | Yoshida | 428/35 |
| 4,872,867 | 10/1989 | Joh . | |
| 4,975,247 | 12/1990 | Badolato et al. | 422/48 |
| 5,013,717 | 5/1991 | Solomon et al. . | |
| 5,039,430 | 8/1991 | Corey, Jr. | 210/806 |
| 5,053,048 | 10/1991 | Pinchuk . | |
| 5,061,738 | 10/1991 | Solomon et al. . | |
| 5,077,372 | 12/1991 | Hu et al. . | |
| 5,163,952 | 11/1992 | Froix | 623/1 |
| 5,272,012 | 12/1993 | Opolski | 428/423.1 |
| 5,342,693 | 8/1994 | Winters et al. | 428/447 |
| 5,395,468 | 3/1995 | Juliar et al. | 156/169 |
| 5,403,341 | 4/1995 | Solar | 606/198 |
| 5,458,616 | 10/1995 | Granger et al. | 606/223 |
| 5,536,582 | 7/1996 | Prasad et al. | 428/450 |
| 5,541,167 | 7/1996 | Hsu et al. . | |
| 5,589,120 | 12/1996 | Khan et al. | 264/130 |
| 5,599,576 | 2/1997 | Opolski | 427/2.3 |
| 5,604,288 | 2/1997 | Furukawa et al. | 524/493 |
| 5,643,580 | 7/1997 | Subramaniam . | |
| 5,702,823 | 12/1997 | Forrestal et al. . | |

OTHER PUBLICATIONS

"Effects of Ultrathin Silicone Coating of Porous Membrane on Gas Transfer and Hemolytic Performance"—Y. Niimi et al. (Artificial Organs, vol. 21, No. 10, 1997, pp. 1082–1086).

Primary Examiner—Corrine McDermott
Assistant Examiner—Cheryl L. Huseman
Attorney, Agent, or Firm—Michael J. Jaro; Harold Patton

[57] ABSTRACT

A method for making a medical device having a biomolecule immobilized on a substrate surface is provided. The method includes coating the substrate surface with an amino-functional polysiloxane; and contacting the amino-functional polysiloxane coated surface with a biomolecule under conditions effective to immobilize the biomolecule.

23 Claims, 4 Drawing Sheets

(A) Non-Modified Polyethylene Surface (B) Amino-Functionalized Polysiloxane-Coated Polyethylene Surface (C) Amino-Functionalized Polysiloxane Coated + Heparin Coupled Polyethylene Surface

METHOD FOR ATTACHMENT OF BIOMOLECULES TO SURFACES OF MEDICAL DEVICES

FIELD OF THE INVENTION

This invention relates to biocompatible materials, and preferably, to blood compatible materials. In particular, this invention relates to a method of making biocompatible, preferably, blood compatible, materials by coating the reaction product of an amino-functional polysiloxane and a biomolecule onto the surface of a biomaterial.

BACKGROUND OF THE INVENTION

The development of vascular grafts and medical devices that contact physiological fluids, particularly blood, is a rapidly developing area of medicine. This has been hampered, however, by the lack of suitable synthetic materials that are stable when contacted with such fluids.

Adverse reactions between materials and blood components are predominant factors limiting the use of synthetic materials that come into contact with physiological fluids. For example, catheters, vascular grafts, and the like, tend to serve as a nidus, or focus, for the formation of thrombi (blood clots). Initial contact of such materials with blood results in deposition of plasma proteins, such as albumin, fibrinogen, immunoglobulin, coagulation factors, and complement components. The adsorption of fibrinogen onto the surface of the material causes platelet adhesion, activation, and aggregation. Other cell adhesive proteins, such as fibronectin, vitronectin, and von Willebrand factor (vWF) also promote platelet adhesion. As a result, the continual use of anticoagulants in conjunction with the introduction of such materials to the body is often necessary.

Furthermore, complement activation occurs when materials are introduced into blood. Adsorption of large amounts of IgG, IgM, and C3b onto surfaces causes activation. Subsequently, complexes may be formed which contribute to undesirable immune responses, such as proteolysis, cell lysis, opsonization, anaphylaxis, and chemotaxis. As a result, these responses render such materials incompatible with the living body.

A number of approaches have been suggested to improve the biocompatibility, and even blood compatibility, of medical devices. One approach has been to modify the surface of the material to prevent undesirable protein adhesion by providing the material with a low polarity surface, a negatively charged surface, or a surface coated with biological materials, such as enzymes, endothelial cells, and proteins. Another approach has been to bind anticoagulants to the surface of biologically inert materials to impart antithrombogenic characteristics to the materials. Still another approach used in the art has been the copolymerization of various phospholipids which are used as coating materials for various substrates. Partial polymeric backbone coatings have also been used in a similar fashion. However, many of these methods can result in a leaching or "stripping off" of the coating.

Some approaches require amination of the substrate surface. For example, U.S. Pat. No. 5,342,693 (Winters et al.) teaches that a siloxane surface must first be functionalized (e.g., with amine groups) in order to attach biomolecules. Additionally, quaternary amines have been bound to polymer surfaces, followed by the binding of heparin thereto. Conversely, heparin has been complexed with a quaternary amine prior to coating the complex onto a polymeric surface. Both of these methods have the disadvantage of being nonpermanent or leachable systems, i.e., the heparin would gradually be lost from the polymer material into the surrounding medium. Furthermore, coated systems generally have limited viability due to the instability of the anticoagulant.

Thus, a need exists for a blood compatible material for use in medical devices that retains antithrombogenic properties, i.e., reduced platelet adhesion and activation, for an extended period of time.

SUMMARY OF THE INVENTION

The present invention provides a method for making a medical device having a biomolecule immobilized on a substrate surface is provided. The method includes coating the substrate surface with an amino-functional polysiloxane; and contacting the amino-functional polysiloxane coated surface with a biomolecule under conditions effective to immobilize the biomolecule. As a result of the present invention, which results in an amino-functionalized polysiloxane on a substrate surface, the substrate is blood compatible, and preferably, also biocompatible.

A "medical device" may be defined as a device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like which are placed into the blood vessels or the heart for purposes of monitoring or repair.

A "biomolecule" is defined as a biologically active molecule.

A "biocompatible" material is one that does not generally cause significant adverse reactions (e.g., toxic or antigenic responses) in the body, whether it degrades within the body, remains for extended periods of time, or is excreted whole. Ideally, a biocompatible material will not induce undesirable reactions in the body as a result of contact with bodily fluids or tissue, such as tissue death, tumor formation, allergic reaction, foreign body reaction (rejection) or inflammatory reaction.

A "blood compatible" material is one that will not induce undesirable reactions in the body as a result of contact with blood, such as blood clotting. This can be demonstrated by reduced platelet adhesion, for example.

DETAILED DESCRIPTION OF THE INVENTION

Figure 1:
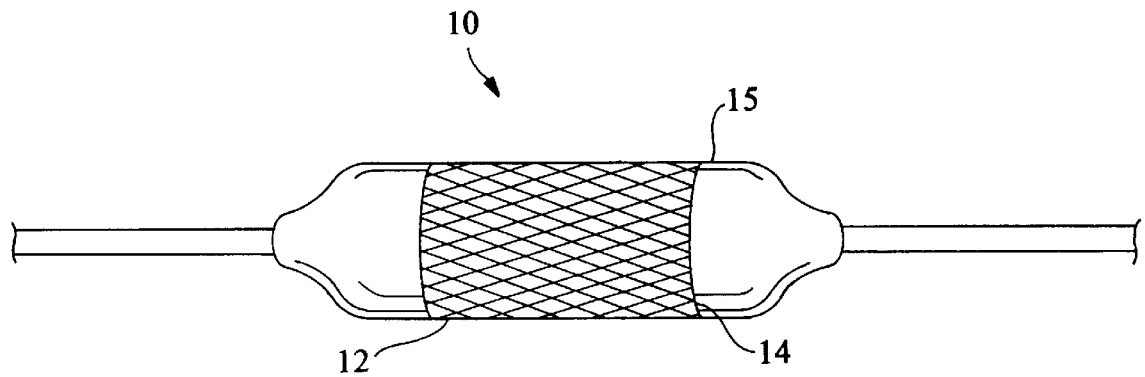
FIG. 1 is an schematic illustration of a stent.

The biocompatibility of materials used in medical devices, which includes implantable materials or materials that are not necessarily implanted but that come into contact with bodily tissues or fluids (e.g., blood), can be improved by covalently attaching a biomolecule, preferably heparin, using an amino-functional polysiloxane. Using this method, the extent and severity of adverse reactions between the substrate and bodily fluids, particularly blood, is reduced.

Blood compatibility is much more complex than the compatibility of a material with other bodily fluids or tissues. This is because of the complex mixture of red cells, white cells, platelets, inorganic ions, and plasma proteins such as albumins, fibrinogens, and globulins in blood. Blood forms a clot or thrombus when injury occurs or when it is contacted by a foreign substance. Almost all materials set off this clot-forming process, and generally soon thereafter become coated with an irreversible clot of varying size. Such clots could have an adverse effect on the utility of such materials. Thus, particularly preferred materials of the present invention are particularly advantageous because they do not cause any significant coagulation or reaction of natural blood components as would occur in vivo, such as blood platelet adhesion and activation.

The materials of the present invention include a substrate and a biomolecule attached via a polysiloxane in an amount and orientation effective to provide an improved nonthrombogenic surface relative to the substrate without the biomolecule and the amino-functional polysiloxane. The contact between blood and a foreign surface initiates a complex process of thrombogenesis that involves platelet adherence, aggregation, and granular release; thrombin generation; and fibrin formation. As a consequence, there are a number of parameters that can be selected as a measure of a material's thrombogenicity. Thus, evaluation of the reactions at the blood-material interface therefore typically involves a multi-parameter (i.e., multi-assay) approach, although one of the assays (e.g., Electron microscopy for platelet adhesion, platelet factor 4 (PF4) assay for platelet activation, thrombin-antithrombin (TAT) assay) used herein can be sufficient to show the improvements resulting from the method of the present invention.

The blood compatibility of the material of the present invention can be demonstrated by reduced platelet adhesion upon interaction with blood when compared to the material without the biomolecule attached via an amino-functional polysiloxane. By this it is meant that for a substrate to which there is a biomolecule, such as heparin, attached through an amino-functional polysiloxane, there is a reduction in the number of platelets attached to the substrate surface per unit area relative to the same substrate without the biomolecule and the polysiloxane attached thereto when contacted with human blood according to the procedure outlined in the Examples. Preferably, the substrate surface of this invention is substantially nonthrombogenic, i.e., it causes little or no platelet adhesion to occur. Herein, a substantially nonthrombogenic substrate has less than about 1% of the surface of the substrate covered by platelets. In contrast, substrates without the biomolecule and polysiloxane attached thereto, as much as 10–15% of the surface can be covered with platelets under the same conditions. This can be demonstrated using electron microscopy.

The materials of the present invention preferably cause little or no platelet activation, in addition to low platelet adhesion, as determined by platelet spread. That is, for substrates to which platelets do adhere, the platelets generally remain rounded and exhibit little or no spreading. Platelet activation can also be determined by the release of Platelet Factor 4. For a substrate to which there is a biomolecule, such as heparin, attached through an amino-functional polysiloxane, there is a reduction in the amount of Platelet Factor 4 released relative to the same substrate without the biomolecule and the polysiloxane attached thereto when contacted with human blood according to the procedure outlined in the Examples. Preferably, this reduction is in an amount of at least about 15%, and more preferably, at least about 20%.

The blood compatibility of the material of the present invention can also be demonstrated by reduced thrombin-antithrombin (TAT) formation upon interaction with blood when compared to the material without the biomolecule attached via an amino-functional polysiloxane. By this it is meant that for a substrate to which there is a biomolecule, such as heparin, attached through an amino-functional polysiloxane, there is a reduction in the number of thrombin-antithrombin (TAT) complexes formed relative to the same substrate without the biomolecule and the polysiloxane attached thereto when contacted with human blood according to the procedure outlined in the Examples. Preferably, this reduction is in an amount of at least about 10%, and more preferably, at least about 25%.

The blood compatibility of the material of the present invention can also be demonstrated by reduced terminal complement complex formation upon interaction with blood when compared to the material without the biomolecule attached via an amino-functional polysiloxane. By this it is meant that for a substrate to which there is a biomolecule, such as heparin, attached through an amino-functional polysiloxane, there is a reduction in the number of terminal complement complexes formed relative to the same substrate without the biomolecule and the polysiloxane attached thereto when contacted with human blood according to the procedure outlined in the Examples. Preferably, this reduction is in an amount of at least about 40%, and more preferably, at least about 70%.

The blood compatibility of the material of the present invention can be demonstrated by reduced elastase formation upon interaction with blood when compared to the material without the biomolecule attached via an amino-functional polysiloxane. By this it is meant that for a substrate to which there is a biomolecule, such as heparin, attached through an amino-functional polysiloxane, there is a reduction in amount of elastase formed relative to the same substrate without the biomolecule and the polysiloxane attached thereto when contacted with human blood according to the procedure outlined in the Examples. Preferably, this reduction is in an amount of at least about 20%, and more preferably, at least about 25%.

According to the present invention, the substrate surface is initially coated with an amino-functional polysiloxane (also referred to as a silicone), typically in a liquid carrier (e.g., an organic solvent). Examples of amino-functional polysiloxanes are disclosed in U.S. Pat. No. 3,574,673 (Schweiger), for example. A preferred such material is an amino-functional polydimethylsiloxane copolymer available from Dow Corning under the trade designation "MDX4-4159." This material is available as a solution containing 50% amino-functional polydimethylsiloxane copolymer in mixed aliphatic (e.g., hexane) and isopropanol solvents.

The amino-functional polydimethylsiloxane is typically used as received, often in a liquid carrier) and coated onto a substrate. The surface is then dried (i.e., removing the liquid carrier and any excess siloxane) and the siloxane cured. These steps can be done by a variety of methods. Preferably, they are carried out in one step by flushing the surface of the substrate with moist air (e.g., greater than 50% relative humidity). The air dries the liquid carrier and removes the excess siloxane. Moisture in the air generates Si—OH groups in the siloxane which then cause condensation and curing reactions within the coating.

The substrate coated with the amino-functional polydimethylsiloxane is then contacted with a biomolecule to be attached thereto. This can be accomplished by a number of methods known to one of skill in the art.

One particularly preferred method is an oxidation method involving the use of periodate. The biomolecule, preferably heparin, is contacted with a periodate in a buffered aqueous solution and allowed to react. This controlled oxidation provides a limited number of reactive aldehyde groups per molecule. The periodate is a water-soluble periodate, preferably, an alkali metal periodate, such as sodium periodate. When the biomolecule is heparin, the amount of periodate used is sufficient to react with no more than two of the sugar units in the heparin molecule (i.e., the basic disaccharide residues constituting the structure of the glycosaminoglycan). If the periodate used is sodium periodate and the heparin used is a commercially available injectable form of heparin (e.g., its sodium salt with activity of 160 units/milligram), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to about 8 can be used. A lower pH (e.g., an acetate buffer at pH 4.5) is preferred if a rapid reaction is desired while a more neutral pH (e.g., a phosphate buffer at pH 6.88) is preferred for a slower reaction with a longer storage life. With the acetate buffer at a pH of 4.5, the reaction should proceed for about 3 hours, while with a phosphate buffer at a pH or 6.88, the reaction should proceed for about 16 hours. If desired, the reacted mixture may then be stored prior to use at about 5° C.

The reacted mixture is diluted and the pH adjusted in order to bring the pH of the mixture to a pH that is favorable for the coupling reaction between the biomolecule and the amino-functional polysiloxane. A mild reducing agent, such as sodium cyanoborohydride, is added to the diluted mixture to effect the reduction of the bonds formed between the reactive aldehyde groups on the oxidized biomolecule and the amine functional groups on the polysiloxane coated on the substrate surface. The substrate surface being treated is then contacted with (e.g., immersed in or flushed with) the diluted mixture at a sufficient temperature and for a sufficient time to complete the reaction (i.e., attach the biomolecule). This time can range from about 30 seconds to about 2 hours at temperatures ranging from about 20° C. to about 60° C. For example, at room temperature (i.e., about 20° C. to about 25° C.), the substrate coated with the amino-functional polydimethylsiloxane can be flushed with a solution of a biomolecule over a period of 30 seconds to 5 minutes for effective biomolecule attachment.

Generally, biomolecules used according to this invention can be, for example: antibacterial and antimicrobial agents; anticoagulant and antithrombotic agents; platelet agents; anti-inflammatories; enzymes; catalysts; hormones; growth factors; drugs; vitamins; antibodies; antigens; nucleic acids; dyes (which act as biological ligands); DNA and RNA segments; and proteins and peptides. The biomolecules can be synthetically derived or naturally occurring. These biomolecules include heparin, prostaglandin $E_1$ (PGE1), ticlopidine, plasmin, urokinase, TPA, polyethylene oxide (PEO), and FUT-175. Heparin inhibits the coagulation of blood by interacting with antithrombin III and thrombin to inhibit the conversation of fibrinogen to fibrin. Ticlopidine and prostaglandin $E_1$ inhibit the activation of platelets. Plasmin, urokinase, and TPA are serin proteases which lyse protein deposits and networks. Polyethylene oxide minimizes protein adsorption, and FUT-175 inhibits contact activation.

The substrates that can be modified by the method of the present invention include materials that are substantially insoluble in body fluids and that are generally designed and constructed to be placed in or onto the body or to contact fluid of the body. The substrates preferably have the physical properties such as strength, elasticity, permeability and flexibility required to function for the intended purpose; can be purified, fabricated and sterilized easily; will substantially maintain their physical properties and function during the time that they remains implanted in or in contact with the body. Examples of such substrates include: metals such as titanium/titanium alloys, TiNi (shape memory/super elastic), aluminum oxide, platinum/platinum alloys, stainless steels, MP35N, elgiloy, haynes 25, stellite, pyrolytic carbon, silver or glassy carbon; polymers such as polyurethanes, polycarbonates, silicone elastomers, polyolefins including polyethylenes or polypropylenes, polyvinyl chlorides, polyethers, polyesters, nylons, polyvinyl pyrrolidones, polyacrylates and polymethacrylates such as polymethylmethacrylate (PMMA), n-Butyl cyanoacrylate, polyvinyl alcohols, polyisoprenes, rubber, cellulosics, polyvinylidene fluoride (PVDF), polytetrafluoroethylene, ethylene tetrafluoroethylene copolymer (ETFE), acrylonitrile butadiene ethylene, polyamide, polyimide, styrene acrylonitrile, and the like; minerals or ceramics such as hydroxapatite; human or animal protein or tissue such as bone, skin, teeth, collagen, laminin, elastin or fibrin; organic materials such as wood, cellulose, or compressed carbon; and other materials such as glass, or the like. Substrates made using these materials can be coated or uncoated, and derivatized or underivatized, prior to being coated with the amino-functional polysiloxane.

Medical devices in which the biocompatible material of the present invention can be incorporated include, but are not limited to, surgical implants, prostheses, and any artificial part or device which replaces or augments a part of a living body or comes into contact with bodily fluids, particularly blood. The substrates can be in any shape or form including tubular, sheet, rod and articles of proper shape.

Various medical devices and equipment usable in accordance with the invention are known in the art. Examples of devices include catheters, suture material, tubing, and fiber membranes. Examples of catheters include central venous catheters, thoracic drain catheters, angioplasty balloon catheters. Examples of tubing include tubing used in extracorporeal circuitry, such as whole blood oxygenators. Examples of membranes include polycarbonate membranes, haemodialysis membranes, membranes used in diagnostic or biosensor devices. Also included are devices used in diagnosis, as well as polyester yarn suture material such as polyethylene ribbon, and polypropylene hollow fiber membranes.

Further illustrations of medical devices include the following: autotransfusion devices, blood filters, blood pumps, blood temperature monitors, bone growth stimulators, breathing circuit connectors, bulldog clamps, cannulae, grafts, implantible pumps, impotence and incontinence implants, intra-occular lenses, leads, lead adapters, lead connectors, nasal buttons, orbital implants, cardiac insulation pads, cardiac jackets, clips, covers, dialators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, batteries, bone cement, breast implants, cardiac materials, such as fabrics, felts, mesh, patches, cement spacers, cochlear implant, defibrillators, generators, orthopedic implants, pacemakers, patellar buttons, penile implant, pledgets, plugs, ports, prosthetic heart valves, sheeting, shunts, umbilical tape, valved conduits, and vascular access devices.

The method of the present invention is particularly applicable to stents. The term "stent" refers to any device capable of being delivered by catheter. FIG. 1 is an illustration of a stent 10 (shown around a balloon 15) treated with the amino-functional polysiloxane and biomolecules according to the present invention. Stent 10 includes lumen wall-contacting surface 12 and lumen-exposed surface (not shown). Where the stent is shaped generally as a tube-like structure, including a discontinuous tube or ring-like structure, the lumen-wall contacting surface is the outside surface of the tube and the lumen-exposed surface is the inner surface of the tube. When in place, the outer surface is in contact with a portion of a wall of a lumen, and the inner surface is in contact with blood. Stent 10 is coated with the amino-functional polysiloxane reacted with a biomolecule, thus forming blood compatible surface 14. Typically, both the lumen wall-contacting surface 12 and the lumen-exposed surface are coated with the amino-functional polysiloxane and biomolecules, although, depending on the materials used to make the stent, only the lumen-exposed surface would need to be. Balloon 15 is positioned adjacent the lumen-exposed surface of the stent to facilitate delivery of the stent.

Other suitable stents include a deformable metal wire stent useful as a stent framework, such as that described in U.S. Pat. No. 4,886,062 (Wiktor), which discloses preferred methods for making a wire stent. Other useful metallic stents include those of U.S. Pat. Nos. 4,733,655 (Palmaz) and 4,800,882 (Gianturco). Other suitable stents include the Palmaz-Schatz coronary stent (Johnson & Johnson Interventional, Warren, N.J.) and stents from memory-shaped metals such as self-expanding nitinol stents including that available under the trade designation CARDIO-COIL from Medtronic, Eden Prairie, Minn., and disclosed in U.S. Pat. No. 5,372,600. Preferred stents for use in this invention should be flexible to navigate lumens during insertion, biocompatible, and reliably expand and embed in the lumen wall.

The method of the present invention also is particularly applicable to blood gas exchange devices, e.g., oxygenators. This includes both sheet and tubular forms of membrane oxygenators, which are well known in the art. In the membrane oxygenator, the blood is separated from direct contact with the oxygenating gas by a membrane, which is disposed within a hollow housing. This membrane is microporous or semipermeable, that is, capable of permitting carbon dioxide and oxygen to permeate through it while at the same time preventing the blood itself from passing therethrough.

There currently are two types of membrane oxygenators. One type, called the flat plate membrane oxygenator, employs one or more thin, flat sheets of microporous membrane. In its most basic form, the flat plate oxygenator has a single sheet of microporous membrane sealed into a housing so as to provide in the housing a first compartment (the "blood compartment") for the flow of blood, and a second compartment (the "gas compartment") for the flow of an oxygenating gas. Each of the compartments is fitted with an inlet and an outlet. Blood flows into and out of the blood compartment and the oxygenating gas flows into and out of the gas compartment. Oxygen passes from the oxygenating gas across the membrane into the blood flowing through the blood compartment. Carbon dioxide passes from the entering blood across the membrane to be entrained in the oxygenating gas. The exiting blood, now reduced in carbon dioxide and enriched in oxygen, is returned to the patient. The membrane would be made blood compatible by exposing the entire surface of the membrane to a suitable amino-functional polysiloxane compound; drying to remove solvent and excess compound; and then exposing it to a biomolecule for a time sufficient to couple the biomolecule to the silicone and form a biocompatible membrane.

The other type of membrane oxygenator is referred to as a hollow fiber oxygenator, and is illustrated in U.S. Pat. No. 4,239,729 (Hasegawa et al). A hollow fiber oxygenator employs a large plurality (typically thousands) of microporous or semipermeable hollow fibers disposed within a housing. These hollow fibers are sealed in the end walls of the housing; the end walls are then fitted with skirted end caps. One end cap is fitted with an inlet, and the other is fitted with an outlet. In the Hasegawa et al. oxygenator, the hollow fibers are aligned in the housing so that their longitudinal axes are generally parallel to the longitudinal axis of the housing. In this device, blood enters through the inlet of one end cap, passes through the lumens of the hollow fibers, and exits through the outlet of the other end cap. Oxygenated gas enters the device through the inlet in the peripheral wall near one end of the device, passes over the outer surfaces of the hollow fibers, and exits the device through the outlet in the peripheral wall near the other end of the device. It will be understood that carbon dioxide diffuses from the blood flowing inside the hollow fibers through the fiber walls into the stream of oxygenating gas. At the same time, oxygen from the oxygenating gas flowing over the outer surfaces of the hollow fibers diffuses through the walls of the hollow fibers into the lumens therof to oxygenate the blood flowing therethrough.

Since the development of this type of oxygenator, other oxygenators comprising hollow fibers have been developed. These oxygenators typically comprise a plurality of hollow fibers disposed within a hollow housing and arranged so that blood typically flows over the hollow fibers and gases typically flow through the hollow fibers. Many configurations are possible as to the direction of fluid flow and the arrangement of fibers. The fibers may be in a linear, circular, or spiral arrangement, for example, or may be wrapped or wound around a core in various configurations. Hollow fiber membrane oxygenators are described, for example, in U.S. Pat. No. 4,975,247 (Badolato, et al) and U.S. Pat. No. 5,395,468 (Juliar, et al).

Hollow fibers suitable for use with oxygenators are made blood compatible, typically by exposing the entire surface (i.e., inside and outside surfaces) of the hollow fibers to a suitable amino-functional polysiloxane; drying with moist air to remove solvent and excess compound; and then exposing it to a biomolecule for a time sufficient to couple the biomolecule to the silicone and form blood compatible hollow fibers.

Figure 2:
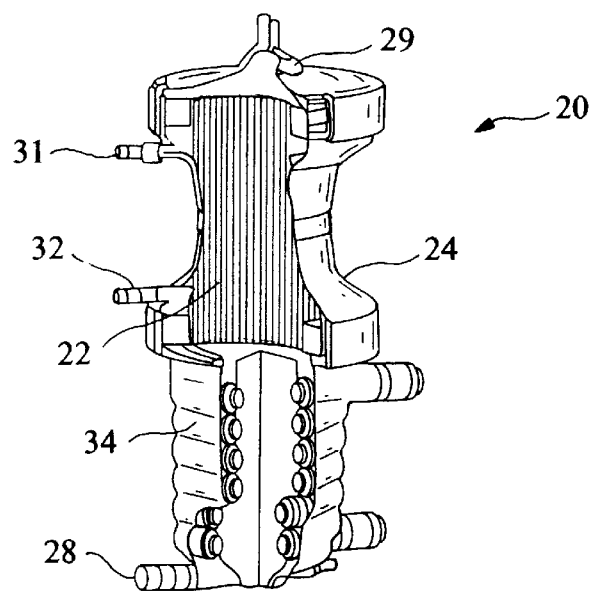
FIG. 2 is an schematic illustration of a blood oxygenator.

FIG. 2 illustrates a simplified diagram of a blood oxygenator 20, wherein a plurality of hollow fibers 22 is disposed within hollow housing 24. Though depicted in a linear arrangement, it is to be understood that the fibers could be arranged in a variety of configurations, including a circular or spiral arrangement, as well as being wrapped around a core or the like. The fibers are supported within housing 24. Blood flow inlet 28 permits the passage of blood through fibers 22. Blood flows through the fibers and out through blood flow outlet 29. Although this figure depicts blood flow through the fibers, it is to be understood that, depending upon the desired characteristics of the oxygenator, blood can flow either through or over the hollow fibers. Gas (e.g., oxygen) flows into housing 24 via gas inlet port 31. The gas flows over the fibers and out of housing 24 via gas outlet port 32.

Although the examples described below involve treatment on polymeric films or tissue culture plates as the substrate surfaces, it is not intended that this invention be so limited.

EXPERIMENTAL EXAMPLES

Immobilization of a Biomolecule

Using a peristaltic pump, the inner surfaces of low density polyethylene (LDPE) tubing (Goodfellow, Cambridge, England; length 5 meters (m), wall thickness 1.1 millimeters (mm), outside diameter 6.4 mm) were cleaned through recirculation of 100 milliliters (mL) of isopropylalcohol (IPA) for 5 minutes. After the IPA was drained from the tubing, the inner lumen was gently flushed with air for about 10 minutes.

The coating process was continued through pumping 100 mL of a 1.5 weight percent (wt-%) amino-functional polydimethylsiloxane (MDX4-4159, available from Dow Corning, Midland, Mich., USA) in hexane (Merck, Darmstadt, Germany) through the tubing for 60 seconds. The inner lumen of the tubing was flushed with moist air (Relative Humidity=50±10%) for 2 hours at ambient conditions.

Periodate heparin stock solution was prepared the day before heparin coupling was carried out (a minimum of 16 hours). Light was excluded from the reaction vessel. Sodium heparin (5 mg/mL) (available from Diosynth, Oss, The Netherlands) was mixed with 0.165 mg/ml $NaIO_4$ (available from Aldrich, Bornem, Belgium) in a 0.05M phosphate buffer (pH=6.88; 0.025 M $Na_2HPO_4$ and 0.025 M $KH_2PO_4$; both available from Merck).

Heparin coupling was performed by pumping through 100 mL of a solution composed of 40 volume percent (vol-%) of the periodate heparin stock solution and 60 vol-% 0.4 M acetate buffer, pH=4.66 (0.2 M glacial acetic acid, 0.2 M sodium acetate; both available from Aldrich Chemical Co., Milwaukee, Wis., USA); after about 10 minutes of recirculation 0.1 milligram per milliliter (mg/mL) $NaCNBH_3$ (Aldrich) was added. Coupling was performed for 2 hours at 50° C. Thereafter the inner lumen was rinsed with deionized water, after which a 1 M NaCl (Merck) solution was pumped through for 10 minutes, after which the inner lumen again was rinsed with deionized water. Finally, the tubing was drained from excess water and flushed with air for 16 hours at ambient conditions.

Blood Testing

Dynamic Blood Loop Testing. Control and surface modified LDPE tubing segments of 50 cenitmeters (cm) each were individually made into a loop by connecting the ends with a 2 cm length of Tygon tubing (Cole Palmer #6408-03); the Tygon tubing was applied such that it would not come in contact with blood. Thereafter the loops were filled with 0.9 wt-% NaCl solution.

A 10 mL syringe was filled with freshly drawn human blood (1 IU/mL heparin), after which blood was inserted in the loop (end volume in the loop is about 6.3 mL), displacing the saline solution. The closed loops were fixed on horizontally positioned acrylic discs in a tank holding warmed 0.9 wt-% NaCl (37° C.). Bood flow was induced by motorized stepwise rotation (in a horizontal plane) of the acrylic discs. After 90 minutes, blood was collected into vials containing EDTA. The vials were centrifuged for 10 minutes at 1500 g (at 4° C.) to obtain the plasma, after which 100 microliter aliquots were frozen at −20° C. until further analysis.

Scanning Electron Microscopy Analysis. After the blood testing, a 2 cm section was removed from the tubing and rinsed 3 times with phosphate buffer, at pH=7.4, after which the tubing samples were stored in 2 mL polypropylene vials containing 2.5% glutaraldehyde at about 4° C. Final sample preparations comprised exposure of the tubing samples to a series of graduated ethanol/water mixtures, to remove water, after which they were critical point dried and gold-coated. Electron microscopy was performed using a JEOL JSM 6301F. Surface area examined on all samples was about 1 $cm^2$.

Thrombin-Antithrombin III Complex (TAT) Generation Assay. Typically, the blood was assayed for generated TAT-complex according to the protocol provided with the reagent-kit for the determination of human thrombin/ antithrombin III complex (ENZYGNOST TAT micro; Behringwerke AG Diagnostica, Marburg, Germany; product no. OWMG 15). In this protocol, blood was withdrawn after incubation and added into microtiter plate wells that were coated with the antibody against thrombin; TAT present in the sample then binds to the antibodies. In a second reaction, peroxidase-conjugated antibodies to human ATIII are bound to the ATIII of the complex. Thereafter the chromogen o-phenyldiamine hydrochloride and then hydrogen peroxide is added. The enzymatic reaction between hydrogen peroxide and chromogen is terminated by the addition of dilute sulphuric acid, after which the absorbance is read at 492 nanometers (nm).

SC5b-9 (TCC) Enzyme Immunoassay. Typically, the blood was assayed for generated Terminal Complement Complex (TCC) according to the protocol provided with the reagent-kit for the determination of SC5b-9 complex (QUIDEL SC5b-9 (TCC) enzyme immunoassay; Quidel, San Diego, Calif., USA). In this protocol, blood is withdrawn after incubation and added into microtiter plate wells that were coated with the monoclonal antibody against the SC5b-9 complex. The trapped SC5b-9 is subsequently detected with horseradish peroxidase (HRP-) conjugated antibodies which bind to the antigens of the SC5b-9 complex. In a third step, a chromogenic enzyme substrate (2-2'-azino-di-(3-ethylbenzthiazoline sulfonic acid) diammonium salt) is added; this salt reacts with the HRP-conjugate to form a green color. The enzymatic reaction is terminated by the addition of oxalic acid, after which the absorbance is read at 405 nm.

Elastase Generation Assay. Typically, the blood was assayed for generated elastase according to the protocol provided with the reagent-kit for the determination of PMN elastase (Merck, Darmstadt, Germany; product no. 12589). In this protocol, blood is withdrawn after incubation and added into microtiter plate wells that were coated with the antibody against human granulocytic elastase; the PMN elastase α Proteinase Inhibitor complex present then binds to said antibodies. In a second stage antibodies marked with alkaline phosphatase are added, which bind to the $\alpha_1$ PI end of the complex. Thereafter the chromogen 4-nitrophenyl phosphate is added. The enzymatic reaction is terminated by the addition of NaOH, after which the absorbance is read at 405 nm.

Enzyme Immunoassay of Platelet Factor 4. Typically, the blood was assayed for generated platelet factor 4 (PF4) according to the protocol provided with the reagent kit (ASSERACHROM PF4 enzyme immunoassay, Diagnostica Stago, Asnieres-Sur-Seines, France). In this protocol, blood is withdrawn after incubation and added into microtiter plate wells that were coated with the antibody against the PF4. The trapped PF4 is subsequently detected with anti-PF4-peroxidase which bind to the free antigenic determinants of the PF4. In a third step, a chromogenic enzyme substrate (ortho-phenylenediamine hydrochloride) is added and then hydrogen peroxide. The enzymatic reaction between hydrogen peroxide and chromogen is terminated by the addition of dilute sulfuric acid, after which the absorbance is read at 492 nm.

Results

The heparinized amino-functional polysiloxane-coated PE surface clearly improves the hemocompatibility and reduces the propensity to inflammation of the surface.

Figure 3:
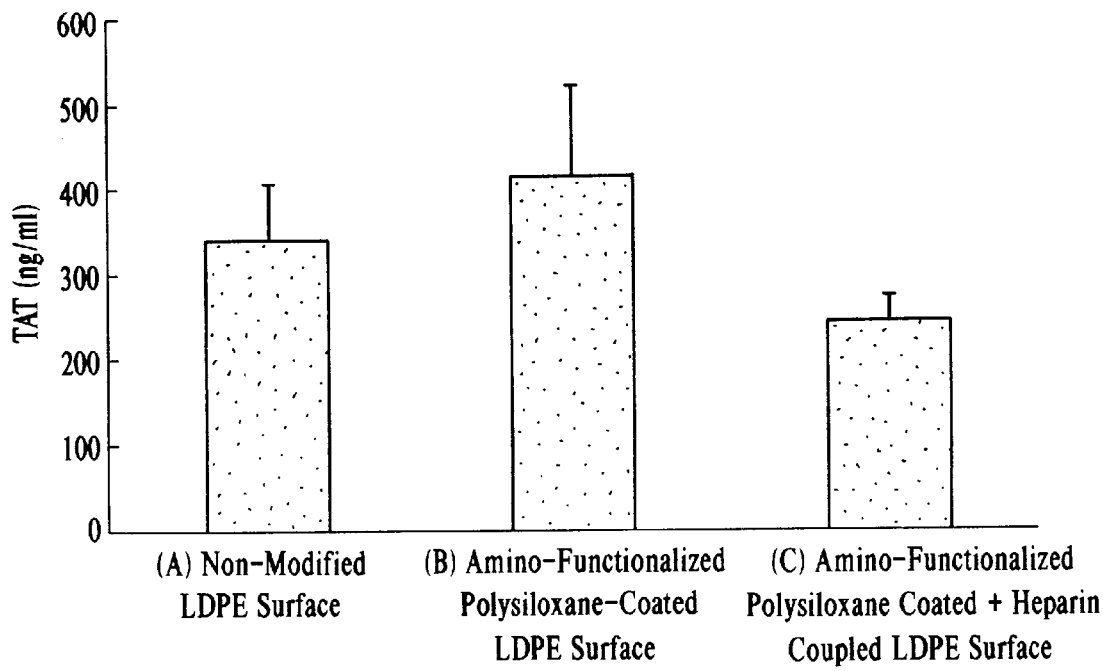
FIG. 3 shows a graph of TAT complex generation (in ng/ml; n=3) after 90 minutes exposure of heparinized (1 IU/ml) human blood to various treated and untreated LDPE surfaces.

FIG. 3 shows a graph of the thrombin anti-thrombin (TAT) complex generation (in ng/mL; n=3) after 90 minutes exposure of heparinized (1 IU/mL) human blood to LDPE surfaces: (a) non-modified; (b) amino-functionalized polysiloxane-coated; and (c) amino-functionalized polysiloxane coated+heparin coupled. Thrombin generation is the result of a sequence of reactions initiated by the contact between blood and a foreign surface. Thrombin itself is rapidly inactivated by the protease inhibitor antithrombin III, so that it may not be detectable; however, the amount of the stable thrombin-antithrombin III (TAT-) complex indicates how much thrombin has been generated. The heparinized amino-functional polydimethylsiloxane-coated surface of this invention showed a significant reduction of thrombin generation, as measured by the TAT-assay.

Figure 4:
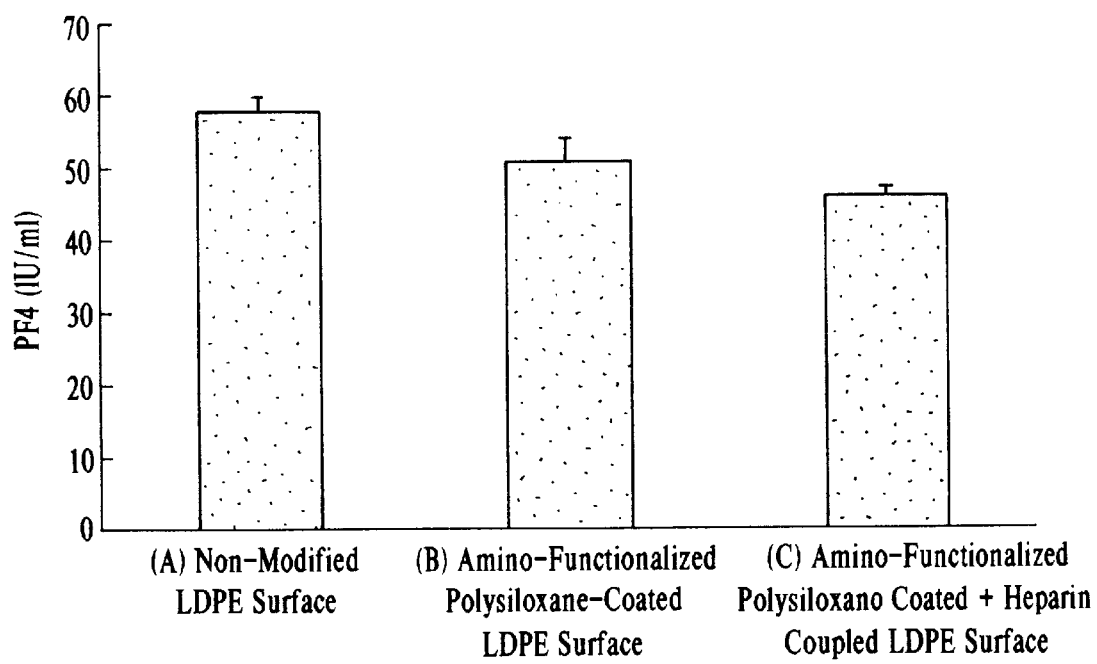
FIG. 4 shows a graph of Platelet Factor 4 release (in IU/ml) after 90 minutes exposure of heparinized (1 IU/ml) human blood to various treated and untreated LDPE surfaces.

FIG. 4 shows a graph of Platelet Factor 4 release (in IU/ml) after 90 minutes exposure of heparinized (1 IU/ml) human blood to LDPE surfaces: (a) non-modified; (b) amino-functionalized polysiloxane-coated; and (c) amino-functionalized polysiloxane coated+heparin coupled. Platelet hyperactivity leads to the release of the contents of the α granules, especially the platelet-specific proteins: β-thromboglobulin and platelet factor 4 (PF4). This platelet activation may result from the interactions with artificial surfaces, but also generated thrombin plays an important role in the activation of platelets. In turn PF4 supports the generated thrombin in preventing heparin from combining with antithrombin III, thus being an obstacle to effective thrombin deactivation. The coated surfaces demonstrated to be less platelet activating, as measured by the PF4-assay, with the heparinized surface being the most platelet friendly surface.

Figure 5A:
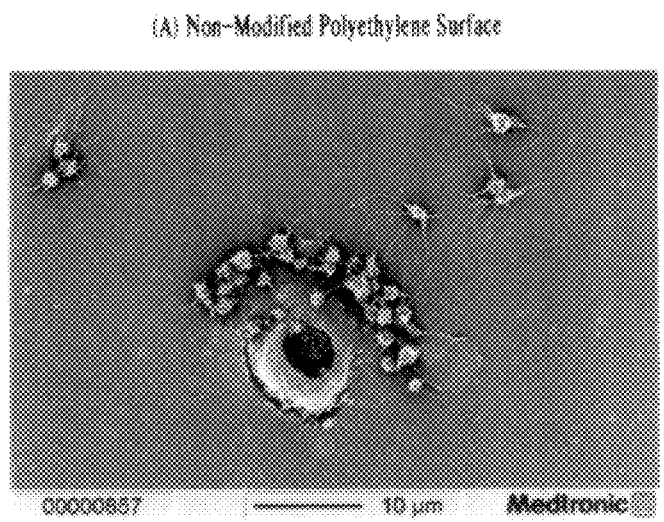
FIG. 5 shows electron photomicrographs of polyethylene surfaces to exposed blood: (a) non-modified; (b) amino-functionalized polysiloxane-coated; (c) amino-functionalized polysiloxane coated+heparin coupled surface.
Figure 5B:
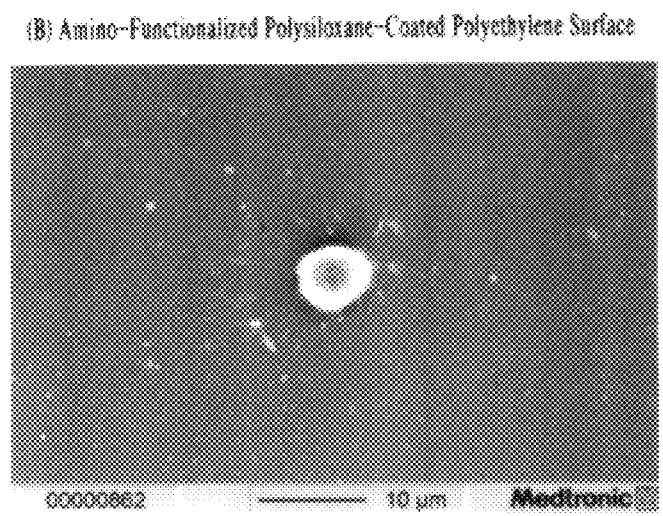
Figure 5C:
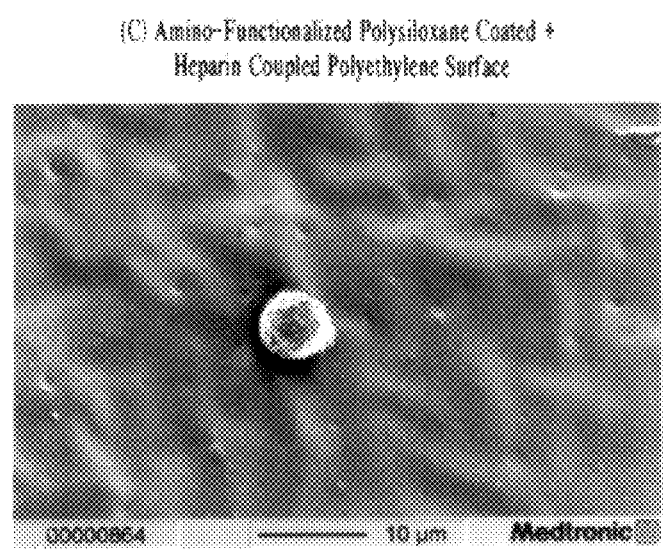

FIG. 5 shows photoelectron micrographs of blood exposed polyethylene surfaces; (a) non-modified; (b) amino-functionalized polysiloxane-coated; and (c) amino-functionalized polysiloxane coated+heparin coupled. Adhesion of platelets is the first event taking place in thrombus formation. Adherent platelets become procoagulant, i.e., the outer membrane serves as a site where enzymatic coagulation complexes are assembled. In the absence of such surfaces clotting is not propagated. Therefore, platelet adhesion is a sensitive parameter in the evaluation of the thrombogenicity of an artificial surface. Platelet adhesion was assayed using electron microscopic analysis of the blood exposed surfaces. Whereas the control LDPE surface demonstrated about 15% surface coverage with platelets (which is less than usual), with apparent presence of activated and spread platelets (FIG. 5a); the amino-functionalized polysiloxane coated LDPE surface significantly reduced platelet adhesion: less than 1% surface coverage was observed, with no apparent activated or spread platelets (FIG. 5b). Additional coupling of heparin did show the same favorable results (FIG. 5c). The observed decrease in adherent platelets does indicate that the heparinized polysiloxane-coated surfaces are less thrombogenic, which in turn is in agreement with the findings of the other tests.

Figure 6:
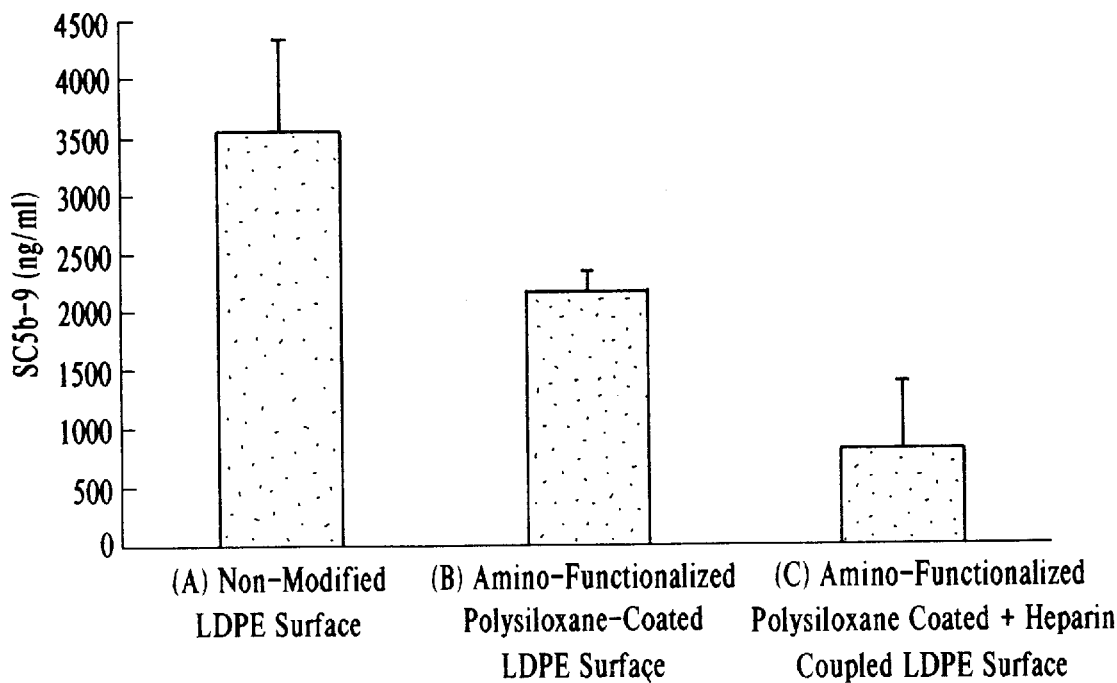
FIG. 6 shows SC5b-9 complex generation (in ng/ml; n=3) after 90 minutes exposure of heparinized (1 IU/ml)human blood to various treated and untreated LDPE surfaces.

FIG. 6 shows a graph of SC5b-9 complex generation (in ng/ml; n=3) after 90 minutes exposure of heparinized (1 IU/ml) human blood to LDPE surfaces: (a) non-modified; (b) modified with amino-functionalized polysiloxane (c) amino-functionalized polysiloxane coated+heparin coupled. The complement system comprises about 20 proteins that circulate in the blood stream. The Terminal Complement Complex (TCC) is generated by the assembly of C5 through C9 as a consequence of activation of the complement system by either the classical or alternative pathway. The membrane attack complex (MAC), which is a form of TCC, is a stable complex and mediates the irreversible target cell membrane damage associated with complement activation. Complexes formed in the absence of a target membrane bind to a naturally occurring S protein. The S protein binds to the nascent C5b-9 complexes at the C5b-7 stage of assembly. The SC5b-9 complex is the soluble, non-lytic form of the TCC. The results obtained after blood was exposed to the (non-)modified LDPE surfaces demonstrate that surface modification per se reduced complement activation; significantly more so, however, with additional heparin coupling (see FIG. 6). These results are considered very favorable, in light of the potential product application of this coating, e.g., cardiopulmonary bypass systems.

Figure 7:
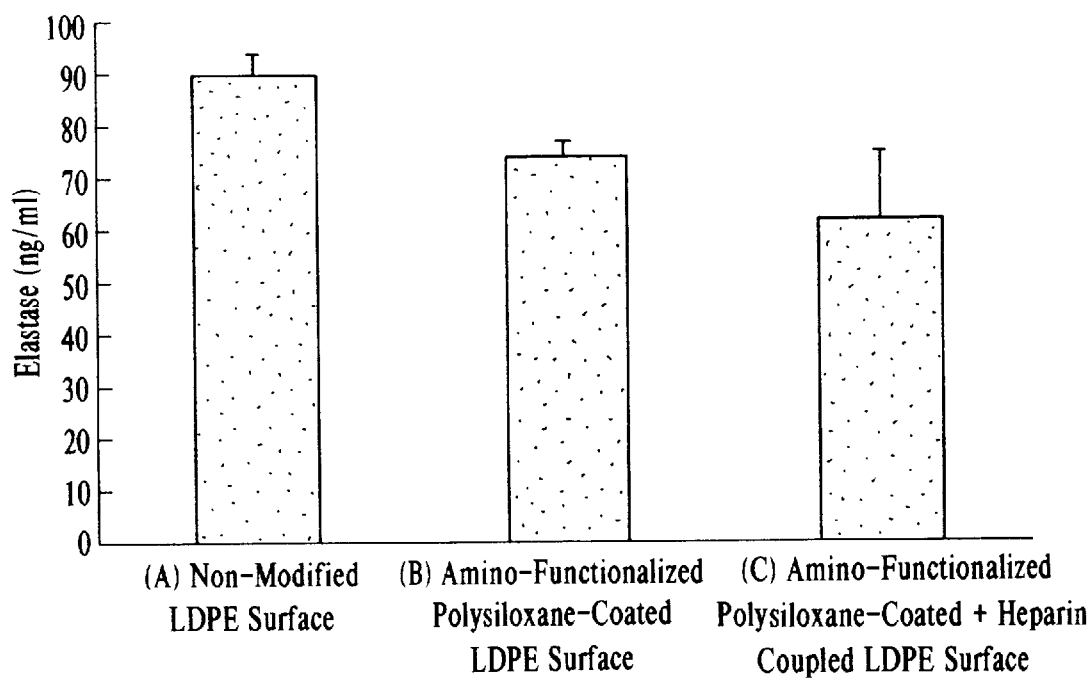
FIG. 7 shows PMN elastase generation (in ng/ml) after 90 minutes exposure of heparinized (1 IU/ml) human blood to various treated and untreated LDPE surfaces.

FIG. 7 shows a graph of PMN elastase generation (in ng/ml) after 90 minutes exposure of heparinized (1 IU/ml) human blood to LDPE surfaces: (a) non-modified; (b) modified with amino-functionalized polysiloxane; and (c) amino-functionalized polysiloxane coated+heparin coupled. Elastase, a neutral proteinase which is contained in peripheral granulocytes, is an additional marker closely related to the material-related inflammatory response. It is known that an intense and persistent inflammatory response induces an increase in steady-state levels of mRNA for IL-1, TNF, and certain other cytokines in peripheral blood monocytes, which potentially may cause remote organ failure or even mortality. In that respect, is the observed decrease in elastase generation with the MDX surfaces, including the heparinized MDX surfaces, considered very favorable (FIG. 7).

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as if each were individually incorporated by reference.

What is claimed is:

1. A method for making a medical device having a biomolecule immobilized on a substrate surface, the method comprising:

coating the substrate surface with an amino-functional polysiloxane; and contacting the amino-functional polysiloxane coated surface with a biomolecule under conditions effective to immobilize the biomolecule.

2. The method of claim I wherein the step of coating the substrate surface comprises:

coating the substrate surface with an amino-functional polysiloxane in a liquid carrier;

removing the liquid carrier; and contacting the amino-functional polysiloxane coating with water to cure the coating.

3. The method of claim 2 wherein the steps of removing the liquid carrier and contacting the coating with water comprises contacting the substrate surface having the amino-functional polysiloxane in a liquid carrier thereon with moist air.

4. The method of claim 1 the step of contacting the amino-functional polysiloxane coated surface with a biomolecule under conditions effective to immobilize the biomolecule comprises contacting the amino-functional polysiloxane coated surface with a biomolecule in a liquid carrier at a temperature of at least about 20° C. for at least about 30 seconds.

5. The method of claim 4 wherein the liquid carrier comprises a periodate in a buffered aqueous solution.

6. The method of claim 5 wherein the periodate comprises an alkali metal periodate.

7. The method of claim 5 wherein the biomolecule comprises heparin and the periodate is present in a sufficient amount to form aldehyde groups on the heparin.

8. The method of claim 7 wherein the buffered aqueous solution has a pH in a range of about 4.5 to about 8.

9. The method of claim I wherein the biomolecule is selected from the group of an antibacterial agent, an antimicrobial agent, an anticoagulant, an antithrombotic agent, a platelet agent, an anti-inflammatory, an enzyme, a catalyst, a hormone, a growth factor, a drugs, a vitamin, an antibody, an antigen, a nucleic acid, a dye, a DNA segment, an RNA segment, a protein, and a peptide.

10. The method of claim 1 wherein the biomolecule is synthetically derived or naturally occurring.

11. The method of claim 1 wherein the substrate is a metal, polymer, ceramic, or glass.

12. The method of claim 1 wherein the surface formed is biocompatible.

13. The method of claim 1 wherein the surface formed is blood compatible.

14. The method of claim 13 wherein the substrate to which there is a biomolecule attached through an amino-functional polysiloxane demonstrates at least a 20% reduction in the amount of elastase formed relative to the same substrate without the biomolecule and the polysiloxane attached thereto when contacted with human blood.

15. The method of claim 13 wherein the substrate to which there is a biomolecule attached through an amino-functional polysiloxane demonstrates at least a 10% reduction in the amount of thrombin-antithrombin complex formed relative to the same substrate without the biomolecule and the polysiloxane attached thereto when contacted with human blood.

16. The method of claim 13 wherein the substrate to which there is a biomolecule attached through an amino-functional polysiloxane demonstrates at least a 15% reduction in the amount of Platelet Factor 4 formed relative to the same substrate without the biomolecule and the polysiloxane attached thereto when contacted with human blood.

17. The method of claim 13 wherein the substrate to which there is a biomolecule attached through an amino-functional polysiloxane demonstrates at least a 40% reduction in the amount of terminal complement complex formed relative to the same substrate without the biomolecule and the polysiloxane attached thereto when contacted with human blood.

18. The method of claim 13 wherein the substrate to which there is a biomolecule attached through an amino-functional polysiloxane has less than about 1% of the surface of the substrate covered by platelets.

19. The method of claim 1 wherein the medical device is a stent.

20. The method of claim 1 wherein the medical device is a blood oxygenator.

21. A method for making a medical device having a biomolecule immobilized on a substrate surface, the method comprising:

coating the substrate surface with a solution of an amino-functional polysiloxane;

drying the amino-functional polysiloxane solution to form a coated surface having amine functionality;

contacting the coated surface with the amine functionality with a biomolecule to form a biocompatible surface.

22. The method of claim 21 wherein prior to the step of contacting the coated surface the method includes a step of combining heparin with a periodate to form an aldehyde-functional heparin.

23. The method of claim 1 wherein the medical device is a blood oxygenator and the substrate being coated includes hollow fibers.

* * * * *